United States Patent [19]

Parks

[11] Patent Number: 4,873,405
[45] Date of Patent: * Oct. 10, 1989

[54] SWITCHING DEVICE

[75] Inventor: Gerald A. Parks, Ames, Iowa

[73] Assignee: Iowa State University Research Foundation, Inc., Ames, Iowa

[*] Notice: The portion of the term of this patent subsequent to Jul. 5, 2005 has been disclaimed.

[21] Appl. No.: 141,824

[22] Filed: Jan. 11, 1988

Related U.S. Application Data

[62] Division of Ser. No. 882,310, Jul. 7, 1986, Pat. No. 4,755,642.

[51] Int. Cl.⁴ .............................................. H01H 15/12
[52] U.S. Cl. .............................. 200/547; 200/DIG. 2
[58] Field of Search ........ 200/153 K, 153 D, DIG. 2, 200/547, 519, 546

[56] References Cited

U.S. PATENT DOCUMENTS

| | | | |
|---|---|---|---|
| 1,025,738 | 5/1912 | Coe, Jr. | 200/61.59 |
| 1,568,509 | 1/1926 | Kolling et al. | 200/61.51 |
| 1,799,651 | 4/1931 | Siegmund | 200/246 |
| 2,411,194 | 11/1946 | DeRome | 200/DIG. 2 |
| 2,604,559 | 7/1952 | Shapiro | 200/52 R |
| 3,900,709 | 8/1975 | Sheesley et al. | 200/5 R |
| 4,486,630 | 12/1984 | Fetchko | 200/52 R |
| 4,517,423 | 5/1985 | Smith, III | 200/DIG. 2 |
| 4,728,812 | 3/1988 | Sheriff et al. | 200/DIG. 2 |

Primary Examiner—Renee S. Luebke
Attorney, Agent, or Firm—Zarley, McKee, Thomte, Voorhees & Sease

[57] ABSTRACT

A switching device for producing a signal in response to small movements between two portions of a surface including a movable member within a housing, the movable member being biased towards a first position by a resilient yet deformable member connected to the housing. A first surface attachment member is connected to the movable member and extends outside of the housing for attachment to the surface. A second surface attachment member is mounted directly to the housing and is attachable to the surface. A switch responsive to sufficient movement of the movable member away from its first position is mounted within the housing adjacent to and in the path of the movable member. The switch is electrically connected to circuitry which can utilize the switching action of the switch which occurs when the surface is moved in such a way that the first and second surface attachment members move with respect to one another, thereby moving the movable member to operate the switch.

7 Claims, 1 Drawing Sheet

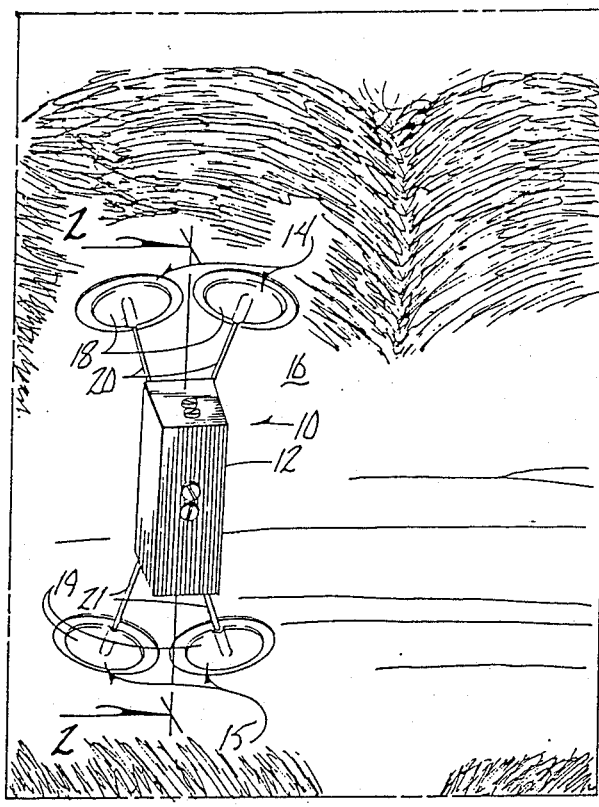
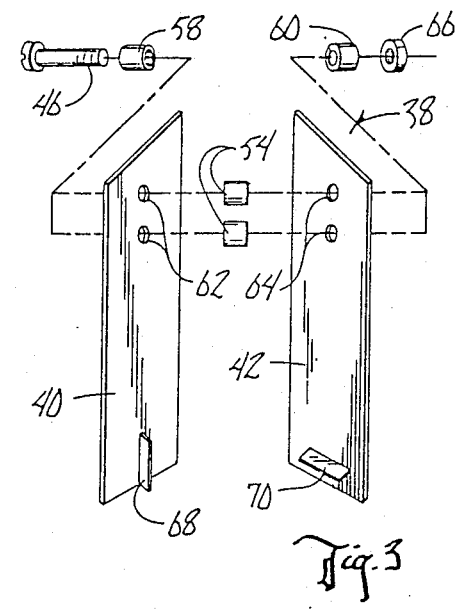
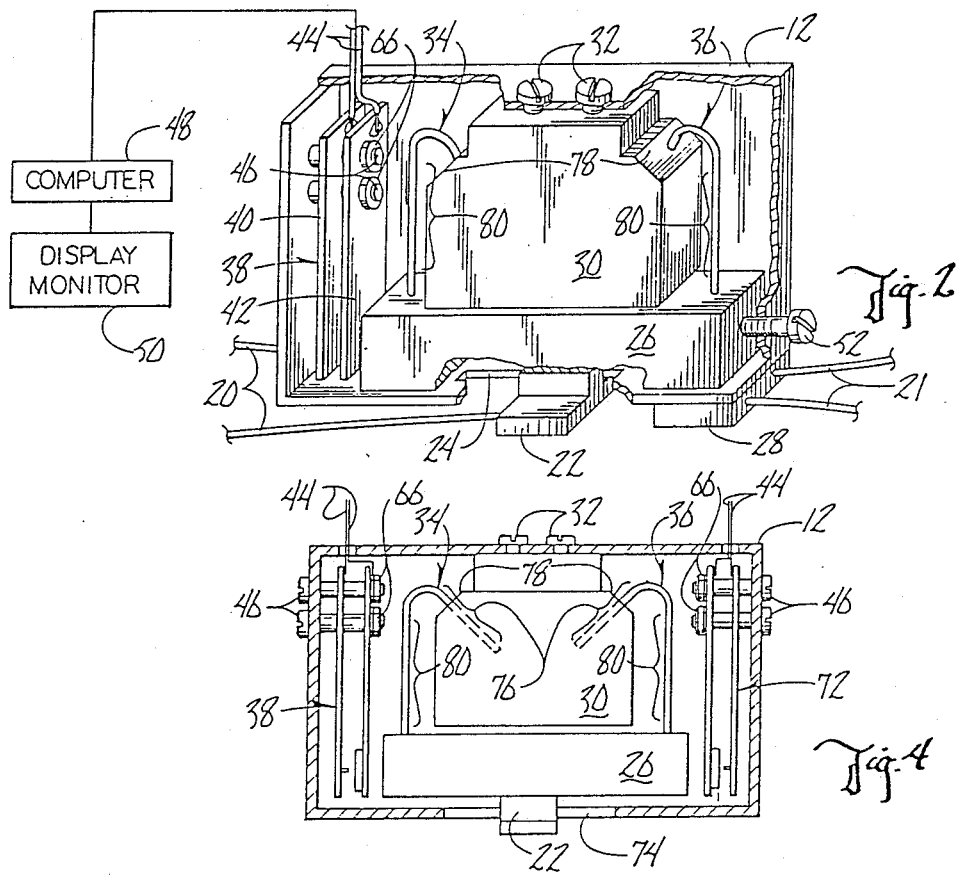
Fig. 1
Fig. 3
Fig. 2
Fig. 4

SWITCHING DEVICE

This is a divisional of copending application Ser. No. 882,310 filed on July 7, 1986, now U.S. Pat. No. 4,755,642.

BACKGROUND OF THE INVENTION

1. Field of the Invention

This application pertains to switching devices, and in particular, a switching device attachable to a surface for producing a signal in response to small movements of two portions of the surface with respect to each other.

2. Problems in the Art

There is a real need for a small, reliable switch which is easily attachable to a surface, and which at the same time is reliably responsive to small movements of two portions of the surface with respect to each other.

Many different types of switching devices exist. However, for applications such as required of the present invention, problems exist in ensuring reliable switching action. Also, it is important that the device be small and lightweight, but at the same time economical to manufacture and durable.

These features are particularly crucial for applications such as utilizing the device for attachment to a person's skin. A primary example of such use would be to allow quadriplegics to communicate better by attaching the device to a movable part of the person's skin, such as on the face. By controlled movement of the skin, the switch can operate to open and close a circuit which can in turn be interfaced with a computer to assist in communication. Use with a computer requires extremely precise electrical contact and, at the same time, assurance that when contact is to be cut off, that no shorting or other complications arise.

It is therefore a primary object of the invention to provide a switching device which improves over and solves the problems and deficiencies in the art.

A further object of the invention is to provide a switching device which is reliable and accurate.

A further object of the invention is to provide a switching device which is easily attachable to a surface and is of small dimensions and lightweight.

Another object of the invention is to provide a switching device which can be easily interfaced with other electronic equipment such as computers.

Another object of the invention is to provide a switching device which is responsive to small movements of two portions of a surface with respect to one another and to which the switching device is attached, yet maintains reliable and accurate switching action.

A further object of the invention is to provide a switching device which is flexible in use, durable, and economical.

These and other objects, features, and advantages of the invention will become more apparent with reference to the accompanying drawings and specification.

SUMMARY OF THE INVENTION

The invention includes a housing holding a movable member suspended by resilient yet deformable means connected to the housing. A switch means is mounted within the housing adjacent to and in the path of movement of the movable member.

Two surface attachment means have portions which are attachable to a surface by use of adhesives, or other means known within the art. A first surface attachment means extends through the housing and is connected to the movable member. The second surface attachment means is mounted directly to the housing.

The switch means is in electrical connection with an electrical circuit. Because the first surface attachment means is connected to the movable member, and the second surface attachment means is connected to the housing, movement of the respective portions of the surface to which the surface attachment means are attached, causes movement of the first and second surface attachment means with respect to one another. The movable member then moves in the housing. If the movement is in the appropriate direction and of an appropriate distance, the movable member causes operation of the switch means which closes the electrical circuit.

More than one switch means can be positioned in the path of the movable member so that multiple switching functions may be possible. Additionally, adjustment means can be utilized with respect to the movable member to adjust its normal position in the housing and with respect to any switch means.

The device can be of a small size, lightweight, and readily adaptable to be interfaced with a computer means. This requires reliable and precise switching action. Likewise, the device is particularly adaptable to be attached to a person's skin and to provide switching signals in response to small movements of the skin. Therefore, the movable member is held within the housing by resilient yet deformable means which allow easy movement of the movable member with minimal friction, while at the same time ensuring precise and repeated movement of the movable member.

BRIEF DESCRIPTION OF THE DRAWINGS

FIG. 1 is a perspective view of the invention schematically depicted attached to the skin of a human's forehead.

FIG. 2 is a cut-away partial perspective and schematic view of a first embodiment of the invention.

FIG. 3 is an exploded perspective view of one type of switch means which can be used with the invention.

FIG. 4 is a partial sectional elevational view of a second embodiment of the invention.

DETAILED DESCRIPTION OF THE PREFERRED EMBODIMENT

In reference to the drawings, and particularly FIG. 1, there is shown a switching device 10 in accordance with the invention. A housing 12 contains the switching elements. Skin attachment means 14 and 15 extend in opposite directions from housing 12. In the embodiment of FIG. 1, switching device 10 is attached to the skin 16 of a human's forehead. Skin attachment means 14 and 15 comprise pads or feet 18 and 19 which, with appropriate adhesive, attach securely to skin 16. Such adhesives are well known within the art and easily used by those of ordinary skill in the art.

Arms 20 and 21 extend respectively from pads or feet 18 and 19 towards housing 12. Movement of skin 16 by the person causes movement of pads 18 of skin attachment means 14 with respect to pads 19 of skin attachment means 15, thereby providing a movement in the skin surface which is translated to a signal by switching device 10.

FIG. 2 depicts one preferred embodiment of the invention. Arms 20 of skin attachment means 14 are rigidly connected to connecting member 22. Connecting member 22 in turn extends through slot 24 into housing 12 and is rigidly connected to a movable member or carriage means 26.

Arms 21 of skin attachment means 15 are rigidly connected directly to a connecting member 28 which is directly secured to housing 12.

A block member 30 is rigidly secured to housing 12 by screws 32 and really is an integral part of housing 12. Movable member 26 is held in a suspended state within housing 12 at a spaced apart position from block member 30 by wire springs 34 and 36. Wire springs 34 and 36 are made of a material that is resilient yet deformable so that movable member 26 is always biased towards what shall be called a normal or first position, such as shown in FIGS. 2 and 4.

However, when skin attachment means 14 moves relative to skin attachment means 15, this in turn causes connecting member 22 to move relative to connecting member 28 and housing 12. As a result, movable member 26 also moves away from the first position. It is allowed to do so because of the deformable nature of wire springs 34 and 36. If connecting member 22 is displaced a sufficient distance away from connecting member 28, movable member 26 will come into contact with leaf switch 38, causing leaves 40 and 42 to come into contact with one another. An electrical circuit would then be closed as leaves 40 and 42 each have a wire 44 electrically connected thereto. Leaves 40 and 42 are electrically insulated from one another and are secured to housing 12 by bolts 46.

As is schematically shown in FIG. 2, wires 44 can be operatively connected to a computer 48 which can be programmed to interpret the switching action of leaf switch 38 to allow visual display of communication or other parameters on a display monitor 50 based on the switching actions of switching device 10. Such interconnections and suitable programming are well within those of ordinary skill in the art.

It is also noted that FIG. 2 shows an adjustment screw 52 threadably mounted through housing 12. Adjustment screw 52 can be made to abut the end of movable member 26 opposite from leaf switch 38 to facilitate the positioning of the normal or first position of movable member 26. Adjustment screw 52 essentially allows adjustment of the sensitivity of switching device 10.

FIG. 3 depicts a preferred embodiment for leaf switch 38. In order to insure reliable and accurate switching action, leaves 40 and 42 are separated by insulating collars 54. Bolts 46 are insulated from leaves 40 and 42 by insulating washers 58 and 60, which extend through apertures 62 and 64. Nuts 66 then removably secure bolts 46 in place and to housing 12. FIG. 3 also shows raised knife edges 68 and 70 which are disposed perpendicularly to one another and positioned so that movement of leaves 40 and 42 towards one another will ensure contact along those accurate edges. This ensures a reliable and accurate electrical contact.

FIG. 4 depicts an alternative embodiment of the invention. A second switch means 72, identical to leaf switch 38, can be mounted to housing 12 at the opposite end of movable member 26. By manufacturing an extended slot 74 in housing 12, switching device 10 can thus produce a switching action regardless of whether connecting member 22 moves to the right or left. Therefore, by referring to FIG. 1, a switching action can be produced whether the skin 16 is contracted or expanded. This also increases the flexibility of device 10 in that two different signals might be produced from the same switch based on different movements of the skin.

FIG. 4 also shows a preferred positioning of wire springs 34 and 36. As can be seen, end portions 76 are anchored through sloped surfaces 78 in the upper portion of block member 30. Wire springs 34 and 36 then extend angularly upward and outward but then are bent so as to extend generally straight downward along the sides of block member 30 to where they are anchored in movable member 26. These vertical straight portions 80 of wire springs 34 and 36 are thus disposed at an acute angle to end portions 76, and generally at a 45° angle. This has been found to be the preferred orientation in the shape of wire springs 34 and 36.

It will be appreciated that the present invention can take many forms and embodiments. The true essence and spirit of this invention are defined in the appended claims, and it is not intended that the embodiment of the invention presented herein should limit the scope thereof.

For example, different types of switches, resilient yet deformable means, and skin attachment means can be utilized, all within the skill of those ordinarily skilled in the art. Different arrangements for suspending the movable member and of connecting the springs to the housing can also be utilized.

The preferred embodiment is directed to attachment of the device to human skin. However, the device can also be attached to any surface and will operate upon sufficient movement of two portions of the surface with respect to one another.

Raised knife edges 68 and 70 can be made of 1/16th inch width gold. This is particularly important if the device is used with a computer as such materials like brass are more susceptible to false connections. Computers are extremely sensitive and gold provides the preciseness needed. The arms 20 and 21 connected to pads or feet 18 and 19 can be made of copper wire encased in plastic. This allows arms 20 and 21 to be deformed according to the position desired. The adhesive used to attach pads or feet 18 and 19 to human skin can be any sufficient substance similar to what is known as Liquid Band-Aid.

Switching device 10 can be utilized with a computer to convert pre-programmed selected long and short switching signals into alphabet letters or other commands. It is contemplated that switching device 10 could even be used to control equipment such as wheel chairs, etc.

It can therefore be seen that the present invention achieves at least all of its stated objectives.

What is claimed is:

1. A switching device for attachment to a human's skin to close and open in response to contraction or expansion of the skin, the switching action producing signals which can be directed to a computer device to produce communications and instructions comprising:
   a block means;
   a carriage means attached to the block means by spring means, said spring means being resilient to bias the carriage means in a first position spaced apart from the block means;
   a first connecting means extending between the carriage means and a first skin attachment means;
   a second connecting means attached between said block means and a second skin attachment means;

at least one switch means positioned adjacent to the carriage means and being responsive to movement of the carriage means away from the first position; so that sufficient movement of the first skin attachment means with respect to the second skin attachment means by contraction or expansion of the skin at or around the first and second skin attachment means causes movement of the carriage means from the first position, in turn causing switching action of the switching means.

2. The device of claim 15 wherein the spring means comprise first and second wire springs anchored in and extending parallelly outwardly from spaced apart positions on the block means, and then returning convergingly towards the block means into the carriage means; holding the carriage means in a spaced apart but substantially parallel position with respect to the block means.

3. The device of claim 2 wherein the spring means are anchored in the block means a distance from one another and from the carriage means so as to maintain the carriage means at a spaced apart position during movement of the carriage means.

4. The device of claim 3 wherein first portions of the springs anchored in the block means and extending parallelly outwardly are angularly disposed with respect to second portions of the springs returning convergingly to the carriage means.

5. The device of claim 4 wherein the first and second portions of each spring generally form an acute angle with respect to one another.

6. A switching device attachable to a surface for producing a signal in response to small movements of first and second portions of the surface with respect to one another comprising:
a block means
at least first and second surface attachment means;
a movable member;
resilient means attached between the movable member and the block means, the resilient means biasing the movable member towards a first position;
a connecting member extending between the movable member and the first surface attachment means;
the second surface attachment means being connected to the block means; and
a switch means positioned adjacent the movable member being responsive to movement of the movable member a distance away from the first position as a result of movement of the first portion of the surface with respect to the second portion of the surface sufficient to move the first surface attachment means with respect to the second surface attachment means; said switch means comprising a first switch means adjacent to and in the path of one end of said movable member, and a second switch means adjacent to and in the path of the opposite end of said movable member so that movement of said movable member in either direction can cause either of the first and second means to operate.

7. The device of claim 6 wherein the surface is the skin of a person.

* * * * *